(12) United States Patent
Brancaccio et al.

(10) Patent No.: US 7,531,714 B2
(45) Date of Patent: May 12, 2009

(54) MELUSIN A MUSCLE SPECIFIC PROTEIN, AS A DRUG TARGET FOR PREVENTION AND TREATMENT OF HEART FAILURE

(75) Inventors: Mara Brancaccio, Saint Vincent (IT); Lorenzo Silengo, Turin (IT); Fiorella Altruda, Turin (IT); Giuseppe Lembo, Mugnano del Cardinale (IT); Luigi Fratta, Casaluce (IT); Guido Tarone, Turin (IT)

(73) Assignee: Universita' Degli Studi de Torino, Turin (IT)

( * ) Notice: Subject to any disclaimer, the term of this patent is extended or adjusted under 35 U.S.C. 154(b) by 274 days.

(21) Appl. No.: 10/538,736

(22) PCT Filed: Dec. 19, 2002

(86) PCT No.: PCT/IT02/00807

§ 371 (c)(1),
(2), (4) Date: Aug. 11, 2005

(87) PCT Pub. No.: WO2004/056176

PCT Pub. Date: Jul. 8, 2004

(65) Prior Publication Data

US 2006/0059577 A1 Mar. 16, 2006

(51) Int. Cl.
*G01N 33/00* (2006.01)
*A01K 67/00* (2006.01)
*A01K 67/033* (2006.01)
*A01K 67/027* (2006.01)
*C12N 15/00* (2006.01)
*C12N 5/00* (2006.01)
*C12N 5/02* (2006.01)
*C07H 21/02* (2006.01)
*C07H 21/04* (2006.01)

(52) U.S. Cl. ................. 800/18; 536/23.1; 435/325; 800/3; 800/9; 800/21

(58) Field of Classification Search ............ None
See application file for complete search history.

(56) References Cited

OTHER PUBLICATIONS

Shai Shaw-Yung et al. Circ Res. Mar. 8, 2002;90(4):458-64.*
Fassler R. et al. J Cell Sci. Dec. 1996;109 ( Pt13):2989-99.*
De Acetis M. et al Cardiac overexpression of melusin protects from dilated cardiomyopathy due to long-standing pressure overload. Circ Res. May 27, 2005;96(10):1087-94.*
Hughes MD et al. Drug Discov Today. Mar. 1, 2001;6(6):303-315.*
Houdebine LM. et al. The methods to generate transgenic animals and to control transgene expression. J Biotechnol. Sep. 25, 2002;98(2-3):145-60.*
Brancaccio et al. 1999, JBC, 274: 29282-29288.*
Doetschmann, 1999, Lab. Animal Sci., 49: 137-143.*
Moens et al., 1993, Development, 119: 485-499.*
Jacks et al., 1992, Nature, 359: 295-300.*
Kuehn et al., 1987, Nature, 326: 295-298.*
Jaenisch, 1988, Science, 240: 1468-1474.*
Murray, et al. 1999, Transgenic Animals in Agriculture, CAB International: Oxon, pp. 58-61.*
Franz et al., 1997, J. Mol. Med., 75: 115-129.*
Hammer et al. 1990, Cell, 6: 1099-1112.*
Cowan et al. 2003, Xenotransplantation, 10: 223-231.*
Hammer et al. 1986, J. of Anim. Sci., 63: 269-278.*
Stone and Vulchanova, 2003, Advanced Drug Delivery Reviews, 55: 1081-1112.*
Jackson et al., 2003, Nature Biotechnology, 21: 635-637.*
Sokol and Murray, 1996, Transgenic Research 5: 363-371.*
Storm et al., 2003, PNAS, USA, 100: 1757-1762.*
Lin and Ying, 2001, Current Cancer Drug Targets, 1: 241-247.*
Oekelen et al., 2003, Brain Research Reviews, 42: 123-142.*
Fenske et al., 2001, Current Opinion in Molecular Therapeutics, 3: 154-158.*
Lowenstein and Castro, 2004, Current Opinion in Pharmacology, 4: 91-97.*
Racay, 2002, Bratisl Lek Listy, 103: 121-126.*
Jakel et al., 2004, Nature Reviews: Genetics, 5: 136-144.*
Oback and Wells, 2002, Cloning and Stem Cells, 4: 147-168.*
Campbell et al., 2005, Reprod. Dom. Anim.,40: 256-268.*
Tian et al. 2003, Reprod. Bio. & Endocrin., 98: 1-7.*
Li et al., 2003, Reprod. Bio. & Endocrin., 84: 1-6.*
McEvoy et al., 2003, Reprod. Supp., 61:167-182.*
Vogel, 2003, Science, 300: 225-227.*
Simerly et al., 2003, Science, 300: 297.*
Flatschart and Sogayar, 1999, Brazilian Journal of Medical and Biological Research, 32:867-875.*
Capecchi, 1989, Trends in Genetics, 5: 70-76.*
Ignelzi et al., 1995, Crit. Rev. Oral Biol. Med. 6: 181-201.*
Brancaccio et al, "Melusin Is a New Muscle-specific Interactor for $\beta_1$ Integrin Cytoplastic Domain", The Journal of Biological Chemistry, vol. 274, No. 41, Oct. 8, 1999. pp. 29282-29288.
Brancaccio et al, Melusin, a muscle-specific integrin $\beta_1$-interacting protein, is required to prevent cardiac failure in response to chronic pressure overload, Nature Medicine, vol. 9, No. 1, Jan. 2003, pp. 68-75.
International Search Report.
Cervenka et al. "Early onset salt-sensitive hypertension in bradykinin $B_2$ receptor null mice" Hypertension 34:176-180 (1999).
Eyestone "Production and breeding of transgenic cattle using in vitro embryo production technology" Theriogenol. 51:509-517 (1999).

(Continued)

*Primary Examiner*—Joanne Hama
(74) *Attorney, Agent, or Firm*—Nixon & Vanderhye P.C.

(57) ABSTRACT

The present invention concerns non-human transgenic animals as model study for human pathologies, being transgenic for having altered melusin expression. The non-human transgenic animals are to be used as models to study heart pathologies and provide therapies thereof, wherein the heart pathologies are heart failure, and in particular diluted cardiomyopathy.

18 Claims, 11 Drawing Sheets

OTHER PUBLICATIONS

Figure 2:
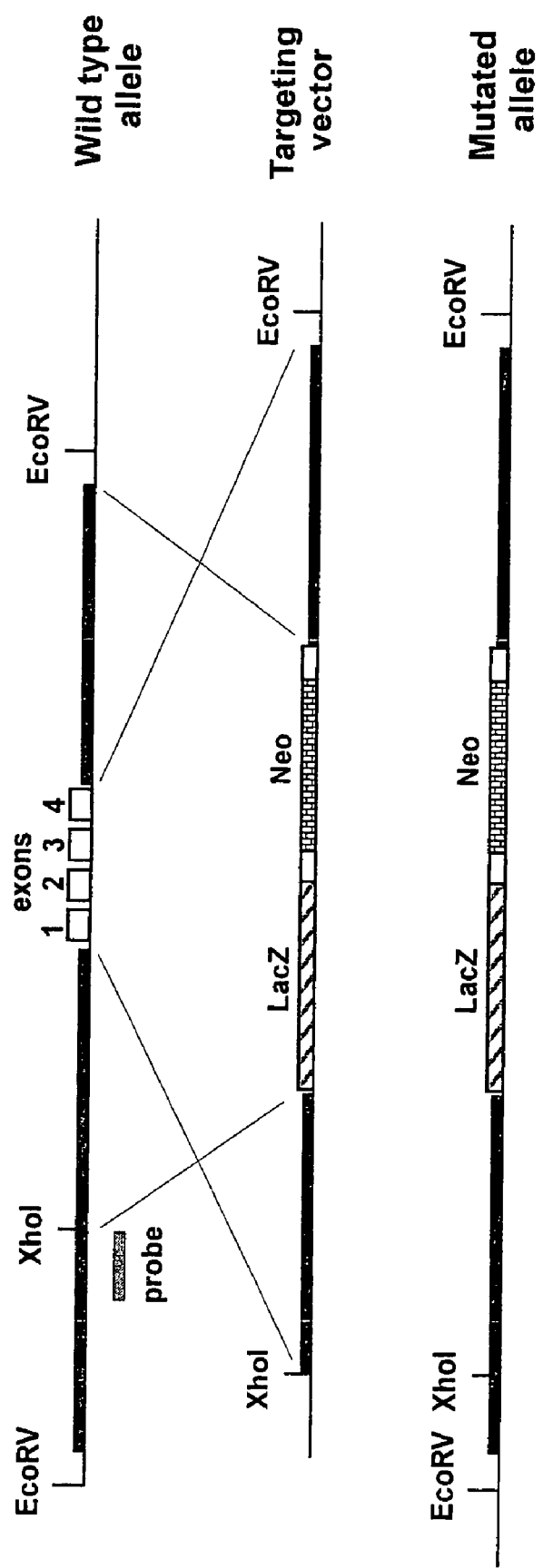

Hirsch et al. "Tissue-specific KO of ECM proteins" Meth. Mol. Biol. 139:147-178 (2000).

Niemann et al. "Expression of human blood clotting factor VIII in the mammary gland transgenic sheep" Transgenic Res. 8:237-247 (1999).

Niemann et al. "Progress in reproductive biotechnology in swine" Theriogenol. 56:1291-1304 (2001).

Rockman et al. "Segregation of atrial-specific and inducible expression of an atrial natriuretic factor transgene in an in vivo murine model of cardiac hypertrophy" Proc. Natl. Acad. Sci. USA 88:8277-8281 (1991).

Strachan et al. "An overview of genetic manipulation of animals" *Human Molecular Genetics*, $2^{nd}$ *Ed.*, Chapter 21, pp. 491-501 (1999).

van Berkel et al. "Large scale production of recombinant human lactoferrin in the milk of transgenic cows" Nat. Biotechnol. 20:484-487 (2002).

Vecchione et al. "Cardiovascular influences of $\alpha_{1b}$-adrenergic receptor defect in mice" Circulation 105:1700-1707 (2002).

Wang et al. "Transgenic goats produced by DNA pronuclear microinjection of in vitro derived zygotes" Mol. Reproduct. Dev. 63:437-443 (2002).

* cited by examiner

Figure 1

```
        1         10        20        30        40        50        60
Mo  MSLLCYNKGCGQHFDPNTNLPDSCRYHPGVPIFHDALKGWSCCRKRTVDFSEFLNIKGCTVGLHCAEKL
    ||||  ||||||||||||||||||  :|||||||||||||||||||||||||||||||||||: | ||||||
hu  MSLLCRNKGCGQHFDPNTNLPDSCCHHPGVPIFHDALKGWSCCRKRTVDFSEFLNIKGCTMGPHCAEKL 70        80        90       100       110       120       130
mo  PEVPPQPEGPATSS-LQEQKPLNTIPKSAETLFRERPKSEMPPKLLPLLISQALGVALEQKELDQEPGA
    ||:|  |||||||| ||||||||||:|||||| ||||||:| ||||| ||||| :||||||||||||||
hu  PEAP-QPEGPATSSSLQEQKPLNVIPKSAETLRRERPKSELPLKLLPLNISQALEMALEQKELDQEPGA 140       150       160       170       180       190       200
mo  GLDNSLIWTGSSCQNPGCDAVYQGPESDATPCTYHPGAPRFHEGMKSWSCCGIQTLDFGAFLAQPGCRV
    ||| ||| ||||||||||||||||||||||||||||||||||||||||||||||||||||||||||||
hu  GLD-SLIRTGSSCQNPGCDAVYQGPESDATPCTYHPGAPRFHEGMKSWSCCGIQTLDFGAFLAQPGCRV 210       220       230       240       250       260       270
mo  GRHDWAKQLPASCRHDWHQTDSVVVLTVYGQIPLPAFNWVKASQTELHVHIVFDGNRVFQAQMKLWGVI
    |||||:|||||||||||||||||:||:|||||||||||||||||||||||||||||||||||||||||
hu  GRHDWGKQLPASCRHDWHQTDSLVVVTVYGQIPLPAFNWVKASQTELHVHIVFDGNRVFQAQMKLWGVI 280       290       300       310       320       330       340
mo  NVEQSSVSLMPSRVEISLVKADPGSWAQLEHPDSLAEKARAGVLLEMDEEESEDSDDDLSWTEEEDEEE
    |||||||  |||||||||||||||||||||||| || |||||||: |||||||:|||||||||||  |||
hu  NVEQSSVFLMPSRVEISLVKADPGSWAQLEHPDALAKKARAGVVLEMDEEESDDSDDDLSWTEE--EEE 350
mo  EEAMGE
    ||||||
hu  EEAMGE
```

Figure 5
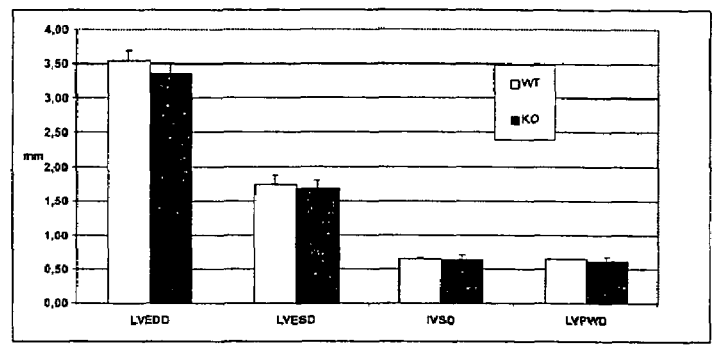
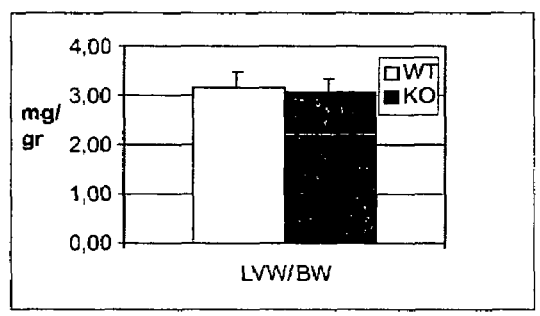
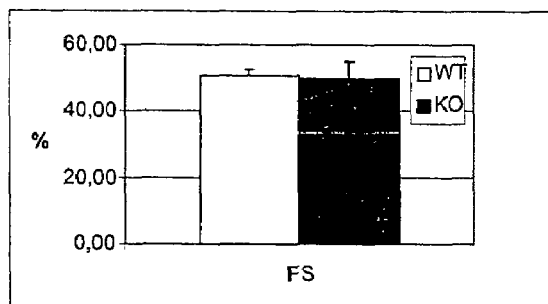
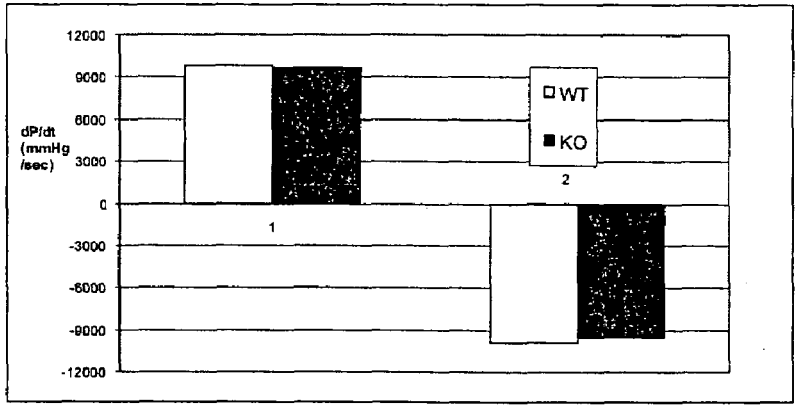

SEQUENCE LISTING

```
<160> NUMBER OF SEQ ID NOS: 2

<210> SEQ ID NO 1
<211> LENGTH: 350
<212> TYPE: PRT
<213> ORGANISM: Mus musculus

<400> SEQUENCE: 1

Met Ser Leu Leu Cys Tyr Asn Lys Gly Cys Gly Gln His Phe Asp Pro
1               5                   10                  15

Asn Thr Asn Leu Pro Asp Ser Cys Arg Tyr His Pro Gly Val Pro Ile
            20                  25                  30

Phe His Asp Ala Leu Lys Gly Trp Ser Cys Cys Arg Lys Arg Thr Val
        35                  40                  45

Asp Phe Ser Glu Phe Leu Asn Ile Lys Gly Cys Thr Val Gly Leu His
    50                  55                  60

Cys Ala Glu Lys Leu Pro Glu Val Pro Pro Gln Pro Glu Gly Pro Ala
65                  70                  75                  80

Thr Ser Ser Leu Gln Glu Gln Lys Pro Leu Asn Thr Ile Pro Lys Ser
                85                  90                  95

Ala Glu Thr Leu Phe Arg Glu Arg Pro Lys Ser Glu Met Pro Pro Lys
            100                 105                 110

Leu Leu Pro Leu Leu Ile Ser Gln Ala Leu Gly Val Ala Leu Glu Gln
        115                 120                 125

Lys Glu Leu Asp Gln Glu Pro Gly Ala Gly Leu Asp Asn Ser Leu Ile
    130                 135                 140

Trp Thr Gly Ser Ser Cys Gln Asn Pro Gly Cys Asp Ala Val Tyr Gln
145                 150                 155                 160

Gly Pro Glu Ser Asp Ala Thr Pro Cys Thr Tyr His Pro Gly Ala Pro
                165                 170                 175

Arg Phe His Glu Gly Met Lys Ser Trp Ser Cys Cys Gly Ile Gln Thr
            180                 185                 190
```

```
Leu Asp Phe Gly Ala Phe Leu Ala Gln Pro Gly Cys Arg Val Gly Arg
        195                 200                 205

His Asp Trp Ala Lys Gln Leu Pro Ala Ser Cys Arg His Asp Trp His
    210                 215                 220

Gln Thr Asp Ser Val Val Leu Thr Val Tyr Gly Gln Ile Pro Leu
225                 230                 235                 240

Pro Ala Phe Asn Trp Val Lys Ala Ser Gln Thr Glu Leu His Val His
                245                 250                 255

Ile Val Phe Asp Gly Asn Arg Val Phe Gln Ala Gln Met Lys Leu Trp
                260                 265                 270

Gly Val Ile Asn Val Glu Gln Ser Val Ser Leu Met Pro Ser Arg
                275                 280                 285

Val Glu Ile Ser Leu Val Lys Ala Asp Pro Gly Ser Trp Ala Gln Leu
    290                 295                 300

Glu His Pro Asp Ser Leu Ala Glu Lys Ala Arg Ala Gly Val Leu Leu
305                 310                 315                 320

Glu Met Asp Glu Glu Ser Glu Asp Ser Asp Asp Leu Ser Trp
                325                 330                 335

Thr Glu Glu Glu Asp Glu Glu Glu Glu Ala Met Gly Glu
                340                 345                 350

<210> SEQ ID NO 2
<211> LENGTH: 347
<212> TYPE: PRT
<213> ORGANISM: Homo sapiens

<400> SEQUENCE: 2

Met Ser Leu Leu Cys Arg Asn Lys Gly Cys Gly Gln His Phe Asp Pro
1               5                   10                  15

Asn Thr Asn Leu Pro Asp Ser Cys Cys His His Pro Gly Val Pro Ile
                20                  25                  30

Phe His Asp Ala Leu Lys Gly Trp Ser Cys Cys Arg Lys Arg Thr Val
            35                  40                  45

Asp Phe Ser Glu Phe Leu Asn Ile Lys Gly Cys Thr Met Gly Pro His
    50                  55                  60

Cys Ala Glu Lys Leu Pro Glu Ala Pro Gln Pro Glu Gly Pro Ala Thr
65                  70                  75                  80

Ser Ser Ser Leu Gln Glu Gln Lys Pro Leu Asn Val Ile Pro Lys Ser
                85                  90                  95

Ala Glu Thr Leu Arg Arg Glu Arg Pro Lys Ser Glu Leu Pro Leu Lys
                100                 105                 110

Leu Leu Pro Leu Asn Ile Ser Gln Ala Leu Glu Met Ala Leu Glu Gln
            115                 120                 125

Lys Glu Leu Asp Gln Glu Pro Gly Ala Gly Leu Asp Ser Leu Ile Arg
    130                 135                 140

Thr Gly Ser Ser Cys Gln Asn Pro Gly Cys Asp Ala Val Tyr Gln Gly
145                 150                 155                 160

Pro Glu Ser Asp Ala Thr Pro Cys Thr Tyr His Pro Gly Ala Pro Arg
                165                 170                 175

Phe His Glu Gly Met Lys Ser Trp Ser Cys Cys Gly Ile Gln Thr Leu
                180                 185                 190

Asp Phe Gly Ala Phe Leu Ala Gln Pro Gly Cys Arg Val Gly Arg His
            195                 200                 205

Asp Trp Gly Lys Gln Leu Pro Ala Ser Cys Arg His Asp Trp His Gln
    210                 215                 220
```

```
                                    -continued
Thr Asp Ser Leu Val Val Val Thr Val Tyr Gly Gln Ile Pro Leu Pro
225                 230                 235                 240

Ala Phe Asn Trp Val Lys Ala Ser Gln Thr Glu Leu His Val His Ile
                245                 250                 255

Val Phe Asp Gly Asn Arg Val Phe Gln Ala Gln Met Lys Leu Trp Gly
                260                 265                 270

Val Ile Asn Val Glu Gln Ser Ser Val Phe Leu Met Pro Ser Arg Val
                275                 280                 285

Glu Ile Ser Leu Val Lys Ala Asp Pro Gly Ser Trp Ala Gln Leu Glu
                290                 295                 300

His Pro Asp Ala Leu Ala Lys Lys Ala Arg Ala Gly Val Val Leu Glu
305                 310                 315                 320

Met Asp Glu Glu Glu Ser Asp Asp Ser Asp Asp Asp Leu Ser Trp Thr
                325                 330                 335

Glu Glu Glu Glu Glu Glu Glu Ala Met Gly Glu
                340                 345
```

MELUSIN A MUSCLE SPECIFIC PROTEIN, AS A DRUG TARGET FOR PREVENTION AND TREATMENT OF HEART FAILURE

This application is the U.S. national phase of international application PCT/IT2002/000807 filed 19 Dec. 2002 which designated the U.S., the entire content of which is hereby incorporated by reference.

FIELD OF INVENTION

The present invention concerns non-human transgenic animals as model study for human pathologies, being transgenic for having altered melusin expression. The non-human transgenic animals are to be used as models to study heart pathologies and provide therapies thereof, wherein the heart pathologies are heart failure, and in particular dilated cardiomyopathy.

In a further embodiment the present invention concerns methods for the development of therapeutical approaches for prevention and treatment of hearth failure, in particular dilated cardiomyopathy, by means of using melusin protein and/or nucleic acids encoding for melusin protein, fragments and/or derivatives thereof.

BACKGROUND OF INVENTION

In subjects affected by arterial hypertension, the left ventricle of the heart is subjected to increased mechanical activity in order to pump blood against increased blood pressure. Under these conditions the heart undergoes a compensatory hypertrophy in which cardiomyocytes increase in size as consequence of increased synthesis and assembly of contractile proteins of actomyosin fibrils.

Although hypertrophy is compensatory and beneficial allowing the generation of more contractile force, under condition of chronic high blood pressure, additional events might occur that either reduce the efficacy of the hypertrophy response or activate additional pathways causing cardiac dilation and progressively leading to heart dysfunction and failure.

The identification of the molecular mechanisms involved in the initial cardiac hypertrophy and in the onset of a subsequent defective cardiomyocytes response is a major challenge of the cardiovascular biology and medicine in these days. In fact, understanding such molecular mechanisms can be of great importance to develop therapeutical strategies aimed to fight congestive heart failure, a pathology that, only in the United States of America, affects more that 400.000 peoples every year.

Considerable efforts have been made in the past decade to identify the molecular mechanisms at the cellular level involved in the hypertrophic response of cardiomyocytes. These studies led to a mechanistic model illustrated in FIG. 10 in which mechanical stretching induced by hemodynamic overload (1) trigger intracellular mechanosensors (2) that activate intracellular signaling pathways (3) leading to hypertrophy by dual modes: by direct activation of muscle specific genes (4a) and by inducing secretion of neurohumoral and autocrine factors (4b) that in turn act on the cardiomyocytes via specific receptors and signaling contributing to the hypertrophic response.

Among the signaling molecules (point 3 of FIG. 10) thought to be involved in the cardiac hypertrophy in response to mechanical overload are: the alfa Gq subunit of the heterotrimeric G protein coupled to the beta adrenergic receptors (Akhter et al. 1998), the phospholipase C beta and protein kinase C, acting downstream of the G proteins (Wakasaki et al. 1997), the Calcineurin/NF-AT3 pathway, the Ras cascade including Raf-1 and ERK1/2 MAP kinases, the stress kinases Jnk and p38, the phosphoinositide 3-kinase, the Jak-STAT pathway (for review see Aoki and Izumo 2001; Ruwhof and van der Laarse 2000; Hunter and Chien 1999). These molecules, although very important in inducing the hypertrophic response, are all acting quite downstream along the signaling pathways.

It is thus clear that identification of the mechanosensors themselves (point 2 of FIG. 10) would be of great importance, since interference with such upstream regulatory elements would allow a much more specific control of the hypertrophic response.

The mechanical tension in the muscle is exerted by the contractile proteins of the cytoskeleton, the actomyosin fibrils which are physically linked to the plasma membrane and to the extracellular matrix, via membrane receptors belonging to the integrin family.

In muscles, integrins are preferentially localized in specific sites known as myotendinous junction and costamers. These are specific sites were actomyosin fibrils are connected to the plasma membrane contributing to a correct and stable association of the contractile machinery to the membrane of the muscle cells.

Besides transmitting the contractile force across the plasma membrane, these junctions are also important mechanosensors capable of transmitting signals inside the cell in response to mechanical stretching. Several proteins are in fact localized at these sites at the cytoplasmic face of the plasma membrane and interacting with integrins. These proteins include paxillin, vinculin, talin, and the tyrosine kinase p125Fak. This molecular machinery is activated by mechanical stretching of the cells (for review see Davis et al. 2001; Carson and Wei 2000) and is the best candidate as the mechanosensing apparatus.

A beta1 integrin isoform (beta1D) that is specifically expressed in striated cardiac and skeletal muscle has been disclosed (Belkin et al 1996). In association with the alpha7 subunit, beta1D forms an heterodimer a7b1D with receptor activity toward merosin (laminin 2) of the extracellular matrix. Functional analysis indicated that beta1D integrin binds both cytoskeletal elements and extracellular matrix ligands with much higher affinity compared to the beta1A isoform present in all non-muscle tissues (Belkin et al 1997) suggesting that beta1D provides a stable actin-laminin interaction across the plasma membrane necessary to support the mechanical tension during muscle contraction.

To further define the molecular basis of these functional properties the inventors searched for proteins capable to bind to the cytoplasmic domain of beta1D. Using the two-hybrid screening the inventors isolated melusin, a novel protein selectively expressed in skeletal muscle and heart (Brancaccio et al. 1999; GenBank AF140690; GenBank AF140691).

Sequence analysis of melusin indicated the presence in the amino terminal half of the protein of a tandem repeated cysteine and histidine rich sequence and of putative binding sites for SH2 and SH3 domains. The C terminal half comprises the binding site for the integrin cytoplasmic domain and is characterized by a stretch of acidic amino acid residues binding to $Ca^{2+}$ (FIG. 1). Melusin is localized at costamers in correspondence of Z line where also integrins and vinculin are concentrated (Brancaccio et al. 1999).

Melusin, thus likely represents a new intracellular transducer of beta1 integrin function in muscle cells.

DESCRIPTION OF THE INVENTION

The invention concerns non-human transgenic animals as model study for human pathologies, being transgenic for having altered melusin expression. Preferably the human pathology is included in the following group: heart failure, dilated cardiomyopathy, hypertensive cardiomyopathy, hypertrophic cardiomyopathy, congestive heart failure, heart infarct. More preferably the human pathology is dilated cardiomyopathy.

In a preferred embodiment the non-human transgenic animal subjected to experimental hypertension conditions, such as for example surgical constriction of the aorta, pharmacological treatment with hypertensive drugs or high sodium diet, exhibits dilated cardiac hypertrophy and contractile dysfunction and is useful as a study model to provide therapies thereof.

It is a further object of the invention cells derivable from the non-human transgenic animal of the invention. The invention concerns different uses of the cells for the selection of molecules pharmacologically effective in triggering melusin activation.

Another aspect of the invention relates to a method for the preparation of a non-human transgenic animal comprising essentially the steps of i) preparing a non-human transgenic animal carrying an inactivated melusin allele; ii) breeding the parent transgenic animal with another non-transgenic animal; iii) selecting transgenic animals heterozygote for the melusin mutation; iv) breeding of the heterozygote animals to select homozygote animals for the melusin gene mutation.

Another aspect of the invention relates to the preparation of a non-human transgenic animal in which the melusin gene is inactivated by genetic approaches distinct from homologous recombination, such as for example antisense RNA or RNA interference approaches in which short RNA sequences complementary to melusin transcript or DNA are used to interfere with either transcription or translation of the melusin gene.

In a further embodiment the present invention concerns methods for the development of therapeutical approaches for prevention and treatment of hearth failure, in particular dilated cardiomiopathy, by means of using melusin protein and/or nucleic acids encoding for melusin protein, fragments and/or derivatives thereof.

In a related aspect, the invention provides methods for identifying chemical compounds that are agonists of melusin, being such agonists in the form of peptides or structural analog organic compounds, which consequently can be used for the manufacture of pharmaceutical compositions for the therapy of heart pathologies.

The present invention relates also to the use of melusin for the manufacture of a medicament for treatment and prevention of hearth pathologies in humans; in particular relates to the use of i) melusin protein, peptides, fragments and/or derivatives thereof, ii) nucleic acids encoding for melusin protein, peptides, fragments and/or derivatives thereof for the preparation of pharmaceutical compositions for the prevention and treatment of heart pathologies.

A further aspect of the present invention relates to proteins able to interact with melusin and acting as downstream transducers of the mechano-chemical signal and leading to the activation of genes of the hypertrophy cardiomyocyte program. Chemical compounds acting as agonist toward such proteins can be utilized as potential drug in the prevention and treatment of hear failure.

According to the present invention, these purposes are achieved by means of the claims which follow.

DETAILED DESCRIPTION OF THE INVENTION

The present invention will now be described in detail with reference to the attached drawings, which are provided purely by way of non-limiting examples and in which:

FIG. 1. Amino acid sequence of Mouse (Mo) and Human (Hu) melusins as deduced from the corresponding cDNAs (murine GenBank AF140691, SEQ ID NO: 1; human GenBank AF140690, SEQ ID NO: 2). Underlined are the cysteine and histidine rich domains (continuous) and the carboxy terminal acidic domain (dotted). Putative binding sites for SH2 and SH3 domains are indicated in bold. The integrin-binding region is boxed. Vertical bars indicate identical amino acids between mouse and human molecules, while double dots are conserved residues. (Brancaccio et al. 1999).

FIG. 2. Genomic DNA construct utilized for the homologous recombination event in ES cells.

Figure 3:
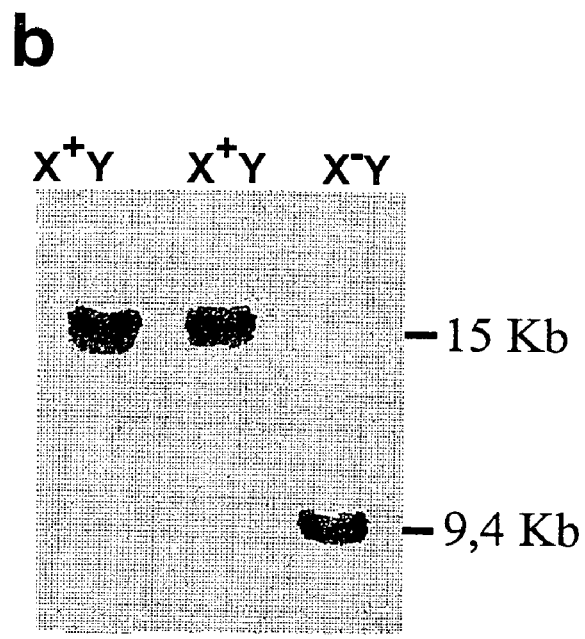

FIG. 3. Southern Blot analysis of the ES cells carrying the mutated melusin gene.

Figure 4:
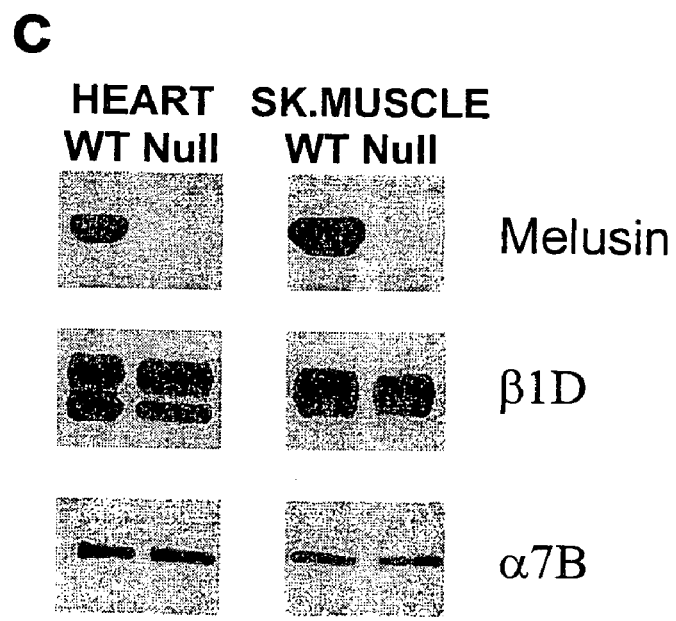

FIG. 4: Western blot analysis of melusin and integrins expression in wild type and mutant mice.

FIG. 5. Echocardiographic and hemodynamic parameters in wild type (WT) and melusin-null (KO) hearts in basal conditions. FIG. 5A, left ventricular end diastolic chamber diameter (LVEDD), left ventricular end systolic chamber diameter (LVESD), interventricular septum thickness in end diastole (IVSD) and left ventricular posterior wall thickness in end diastole (LVPWD). FIG. 5B left ventricular weight expressed as mg per gr of body weight (LVW/BW). FIG. 5C, fractional shortening (FS) of left ventricle calculated as [(LVEDD-LVESD)/LVEDD]×100. FIG. 5D, left ventricular pressure measured in anesthetized mice by a French high fidelity catheter-tip micro manometer (Millar Instrument).

Figure 6:
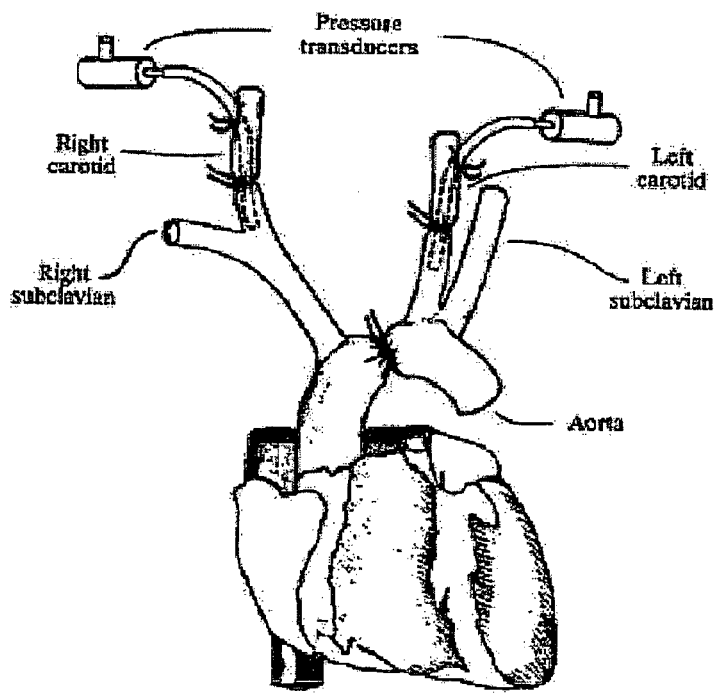

FIG. 6. Scheme of the surgical constriction of the transverse aorta (TAC) utilized to induce pressure overload.

Figure 7:
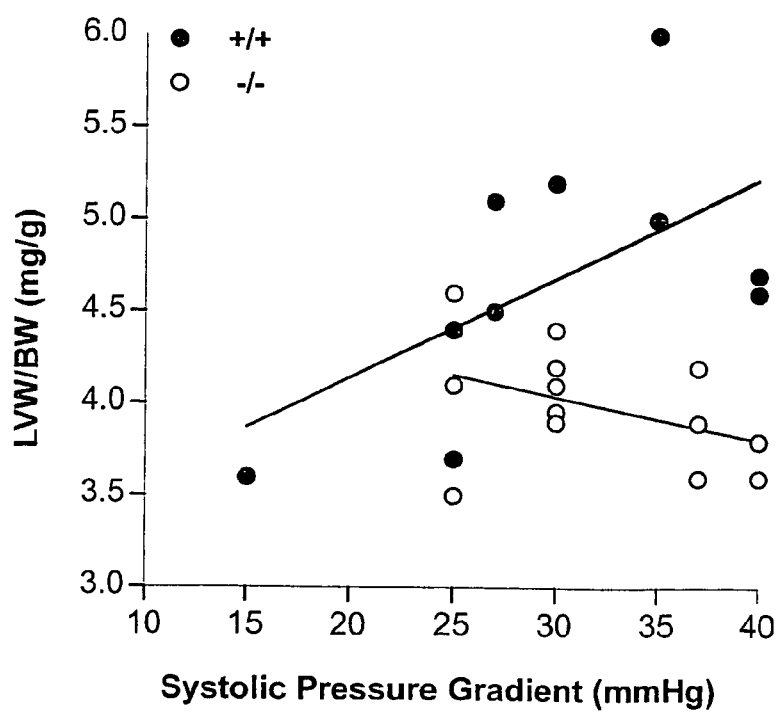

FIG. 7. Left ventricle growth response to transverse aortic constriction in wild type (+/+) and mutant mice (−/−).

Figure 8:
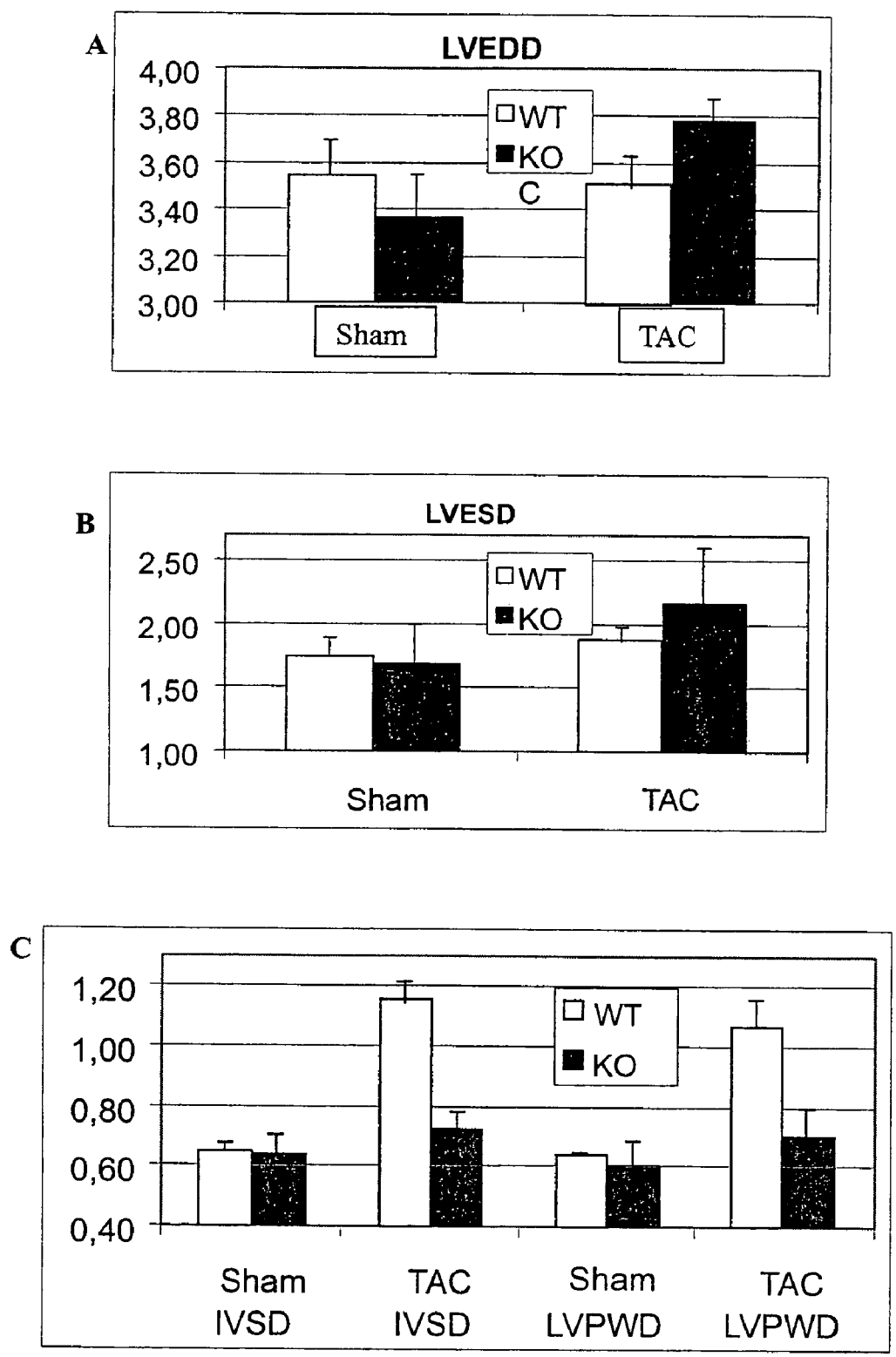

FIG. 8. Echocardiographic parameters in wild type (WT) and melusin-null (KO) hearts of control mice (Sham) or mice subjected to transverse aortic constriction (TAC). FIG. 8A, left ventricular end diastolic chamber diameter (LVEDD). FIG. 8B, left ventricular end systolic chamber diameter (LVESD). FIG. 8C, interventricular septum thickness in end diastole (IVSD) and left ventricular posterior wall thickness in end diastole (LVPWD).

Figure 9:
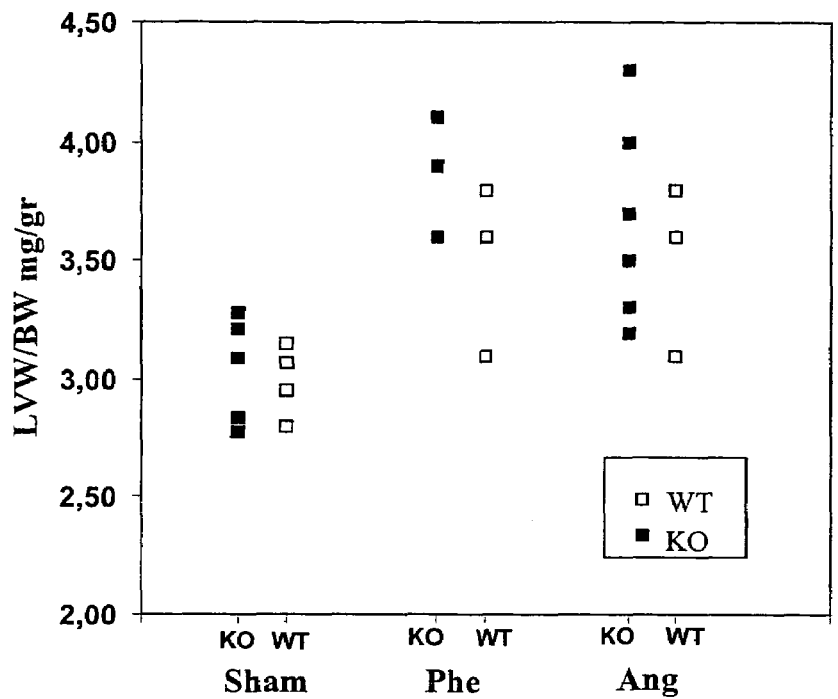

FIG. 9. Left ventricle growth response to sub-pressor doses of phenylephrine and angiotensin II. Cardiac hypertrophy was evaluated by left ventricular/body weight ratio as indicated on the Y-axis. −/− and +/+ indicate the mutant (black squares) and wild type (empty squares) mice respectively.

Figure 10:
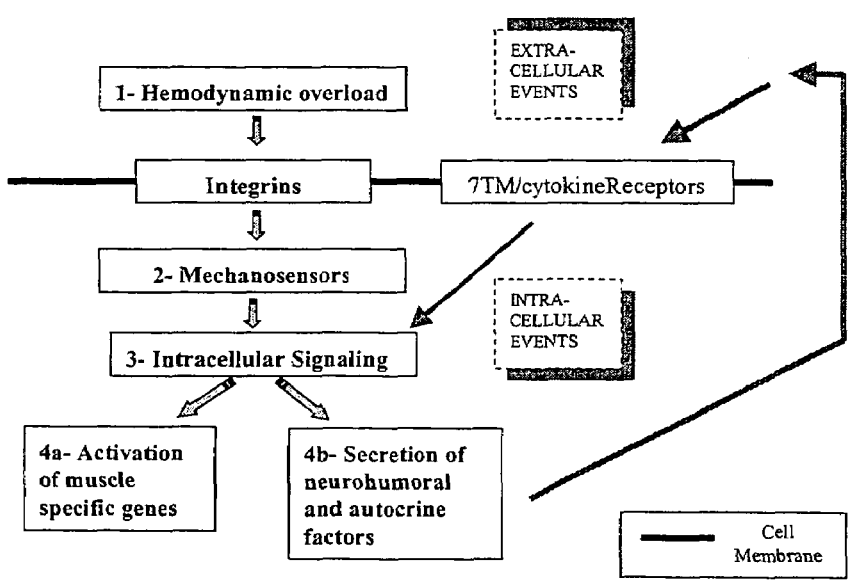

FIG. 10. Diagrammatic representation of the molecular mechanism at the cellular level involved in hypertrophic response of cardiomyocytes.

Figure 11:
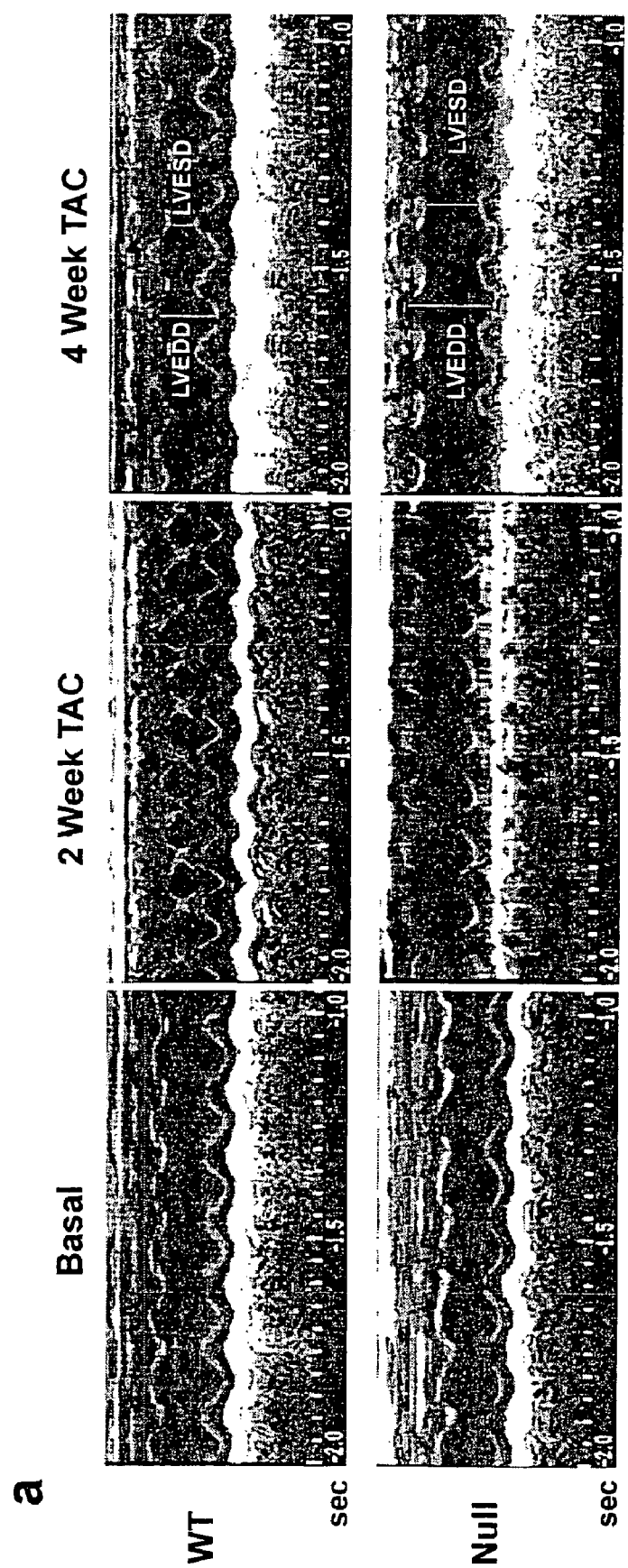
Figure 11:
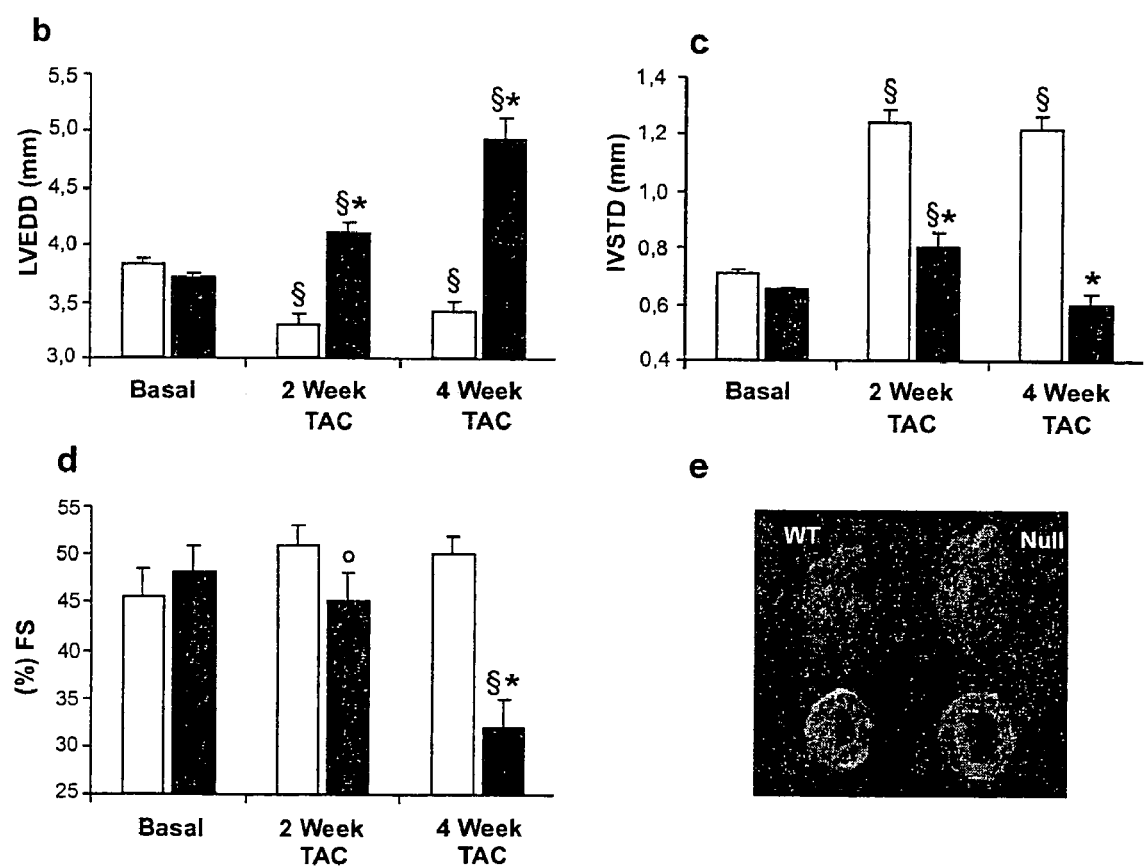

FIG. 11. Left ventricle remodeling and function after 2 and 4 weeks from TAC in wild-type (WT, empty bars) and mutant mice (KO, filled bars). FIG. 11a: Representative M-mode left ventricular echocardiografic recording of wild-type (upper pictures) and melusin-null (lower pictures) mice. FIG. 11b: Left ventricular end diastolic diameter (LVEDD). FIG. 11c: interventricular septum thickness in end-diastole (IVSTD). FIG. 11d: percent fractional shortening (% FS) as parameter of left ventricle contractile function. FIG. 11e: Representative gross morphology of whole hearts (upper rows) and transversal sections at base level of the left ventricles of wild-type and melusin-null mice after 4 weeks from TAC. §: P<0.01 vs Basal; *: P<0.01 vs wild-type; °: P<0.05 vs wild-type.

Figure 12:
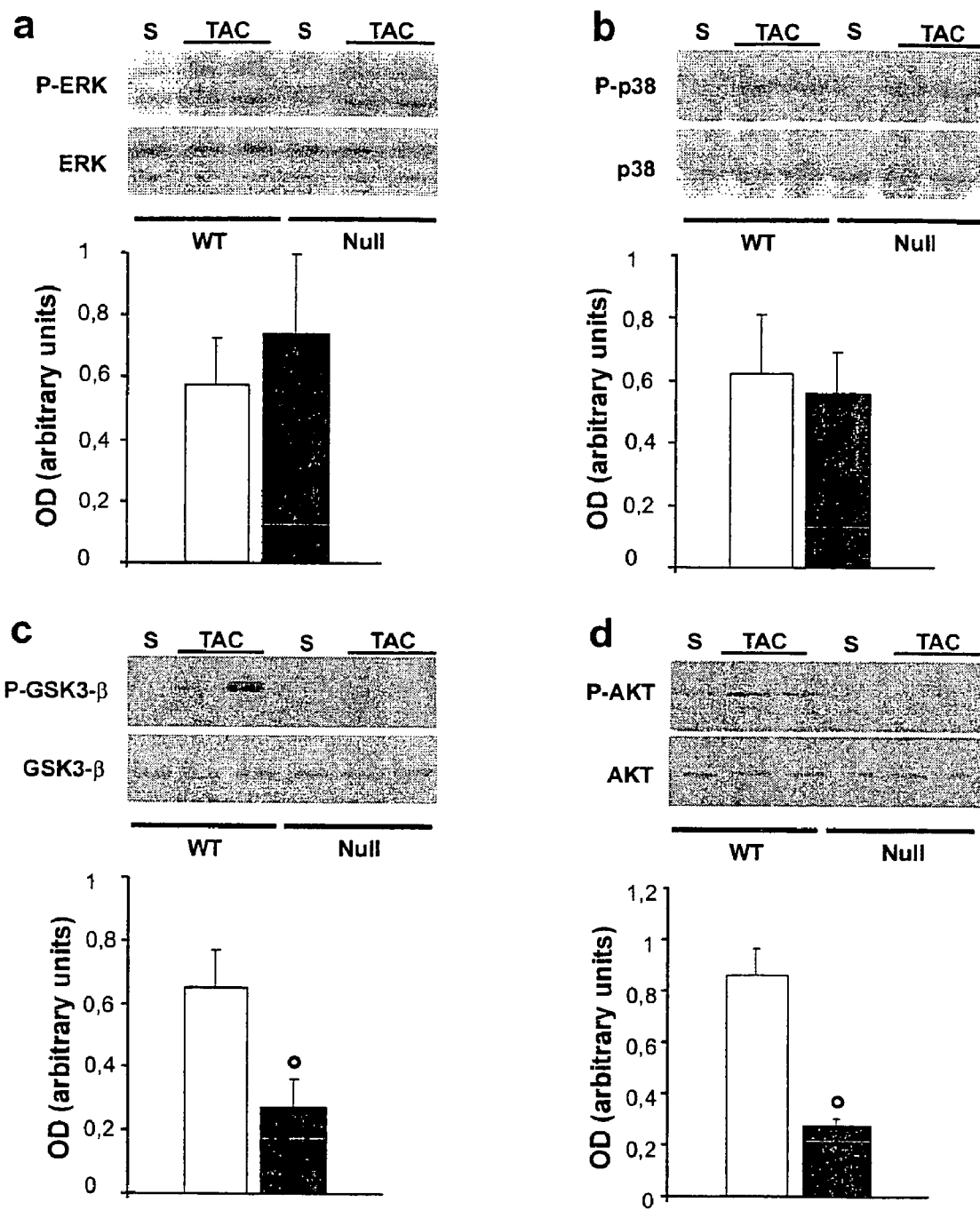
Figure 12:
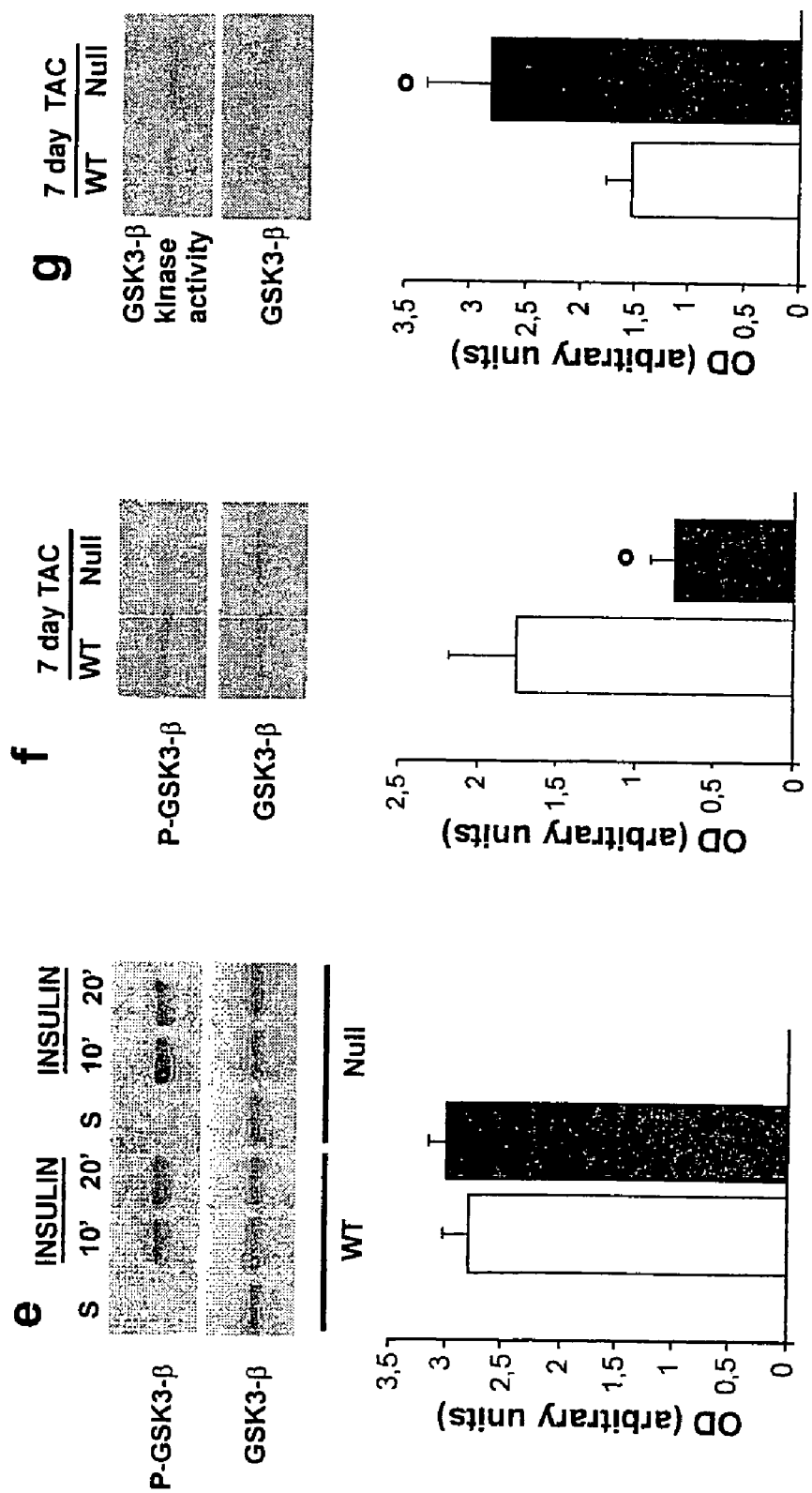

FIG. 12. Impaired GSK3β phosphorylation in melusin-null mice in response to TAC by comparison of results between Wild-type (WT, empty bars) and melusin-null mice (KO, filled bars). Left ventricle protein extracts were analyzed by western blotting with antibodies to phosphorylated signaling molecules. Sample loading was controlled using antibodies specific for each protein. The intensity of the bands from two independent experiments with a total of 8 mice for group was measured and relative intensity was calculated after subtraction of basal level in sham operated animals. ERK (FIG. 12a), p38 (FIG. 12b), GSK3β (FIG. 12c), AKT (FIG. 12d) are rapidly phosphorylated in response to TAC in wild-type mice, but phosphorylation of GSK3β and AKT were strongly impaired in melusin-null mice. GSK3β was phosphorylated to a comparable level in both wild-type and melusin-null mice 10 and 20 min after IP injection of 2 IU of insulin (FIG. 12e). Reduced serine9-GSK3β phosphorylation (FIG. 12f) and increased kinase activity (FIG. 12g) were detected in melusin-null hearts subjected to 7 days of TAC. °: P<0.05 vs wild-type.

The present invention will now be described in relation to some preferred embodiments by way of non-limiting examples.

As it will be apparent from the results described below, melusin plays a crucial role in the mechano-chemical signaling leading to a correct cardiomyocytes hypertrophy in response to pressure overload.

In the absence of melusin, cardiac hypertrophy is severely impaired and left ventricle undergoes dilation, thinning and displays reduced contractile capacity, thus becoming unable to withstand the biomechanical stress imposed by the high blood pressure.

Stimulating melusin function and signaling will expectedly improve cardiomyocytes hypertrophy preventing dilation and subsequent heart failure. Therapeutic strategies will, thus, involve expression or over-expression of melusin in failing hearts by gene transfer, use of drugs acting as agonists of melusin or of melusin downstream effector molecules.

Although several molecules such as the alfa Gq subunit, the phospholipase C beta, the protein kinase C, calcineurin, NF-AT3, Ras, Raf-1, ERK1/2, Jnk and p38MAP kinases, the phosphoinositide kinase 3 and the STATs (see discussion above) are potential targets for drugs aimed to stimulate heart hypertrophy, all these proteins have the great disadvantage of being ubiquitously expressed in most, if not all, tissues. A drug regulating any of these proteins will, thus, unavoidably cause deleterious side effects. Melusin, being a muscle specific protein, will not present this problem and, on the contrary, represents an ideal target molecule for such type of drugs. A second important advantage of melusin over other proteins involved in the heart hypertrophy is its role as mechanosensor, which places melusin in the very early steps of the biochemical signaling cascade triggering the hypertrophic response. Thus, regulating melusin function allows a very specific control of the heart response.

The non-human transgenic animals in which the melusin gene is inactivated by homologous recombination or by genetic approaches different from homologous recombination represent a unique animal model for testing drugs aimed to prevent heart failure. In fact, these animals do not show functional heart defects in basal conditions during their lifespan. Heart failure become apparent only when transgenic animals and more preferably melusin-null transgenic mice are exposed to chronic hypertensive conditions. In a preferred embodiment the hypertensive conditions are determined by surgical constriction of the aorta, pharmacological treatment with hypertensive drugs or high sodium diet. In these conditions, the transgenic mice develop heart dilation and failure with a relatively slow kinetics (within 4 weeks), a time course much slower compared to that shown by other animal models for dilated cardiomyopathy (Arbet et al 1997; Hirota et al 1999; Badorff et al 2002) allowing to more accurately test drugs aimed to prevent cardiac failure.

The preparation of a non-human transgenic animal—preferably melusin-null transgenic animal—comprises essentially the steps of: i) preparing a genomic DNA construct abrogating melusin expression and suitable for homologous recombination event; ii) use of such DNA construct to induce homologous recombination in embryonic stem cells; iii) use of stem cells carrying an inactivated melusin gene to generate a chimeric embryo; iv) selecting animals heterozygote and homozygote for the melusin mutation by breeding the chimeric animals with different mouse strains.

A transgenic animal for melusin is an animal in which the expression of the melusin protein has been altered/modified either in a positive or negative direction by stable or transient introduction in some or all cells of the animals of molecules capable to modify melusin expression at transcriptional, translational or post-translational level.

As a non limiting example a DNA construct coding for an antisense melusin transcript can be used. Expression of such DNA construct is directed by a cardiac specific promoter such as the promoter of the a-myosin heavy chain. This construct is introduced in fertilized oocytes that are then reimplanted in the uterus of foster mothers in order to generate non human transgenic animals that express either none or reduced level of melusin in heart. A second non limiting example consists in the use of vectors coding short duplex RNAs of 21-23 nt capable to silence genes containing homologous sequences (Hasuwa et al., 2002).

The cardiac pathology displayed by the melusin-null transgenic mice described in the present invention indicates that melusin is required to sustain the compensatory hypertrophic response when the heart is exposed to pressure overload. It is thus concluded that the inhibition of melusin function by natural or synthetic compounds can lead to cardiac failure and dilation in animals carrying wild type melusin genes and exposed to hypertensive conditions.

EXAMPLES

Example 1

Production of Melusin-Null Trangenic Mice and Molecular Characterization

To investigate the role of melusin in integrin function the inventors have generated a mutation in mice (inbred 129SV strain) that abrogate melusin expression. Using the murine cDNA (Brancaccio et al. 1999; GenBank AF140691) the present inventors isolated a genomic fragment of 14.8 Kb encompassing four exons at the 5' end of the melusin gene. Partial characterization by restriction map and sequencing indicated that the first exon contains the ATG start codon. A PstI fragment containing exons 1 to 4 was replaced with a cassette containing IRES sequences linked to the LacZ gene followed by the neomycin resistance gene driven by a PGK promoter (FIG. 2). This construct, which has two arms of 4.1 and 5 Kb homologous to the endogenous gene, was electroporated in embryonic stem R1 cells from male 129SV inbred mice. Different clones in which homologous recombination occurred have been identified by Southern blot analysis (FIG. 3). Since the melusin gene is located on the X chromosome (Brancaccio et al 1999) and the ES R1 cells are of male origin, a single homologous recombination event was sufficient to inactivate the melusin gene (FIG. 3). After injection of the mutant ES cells into blastocysts and implant in the uterus of a foster mother, chimeric mice in which the genetically modified cells have colonized the germ line were obtained. Chimeras were than breed with 129SV mice to obtain melusin-null 129SV mice.

The melusin-null mice are viable and fertile and do not show appreciable muscle or heart defects up to 18 months of age.

The successful inactivation of the melusin gene was demonstrated by analysis of protein expression both in heart and skeletal muscles of mutant mice (FIG. 4). These data indicate, thus, that melusin is not required for muscle and heart development.

Example 2

Role of Melusin in Cardiac Hypertrophy

Basal cardiac morphology and performance was investigated by echocardiography and cardiac catheterization and found to be comparable in wild type and melusin-null mice.

As shown in FIG. 5A echocardiography allowed to measure left ventricle end-diastolic (LVEDD), end-systolic diameter (LVESD), interventricular septum thickness in end diastole (IVSD), left ventricle posterior wall thickness in end diastole (LVPWD) and fractional shortening (FS) (FIG. 5C). Left ventricle mass (LVW/BW) was also measured as hypertrophy parameter and found to be comparable in melusin-null and control mice (FIG. 5B). In addition the pressure developed by the left ventricle was directly measured by catheterization with a micro manometer and reported as dP/dt (FIG. 5D). Thus the absence of melusin does not affect cardiac function under physiological conditions.

Melusin deficiency, however, affects cardiac muscle function when hearts are exposed to pressure overload. To analyze the ability to respond to biomechanical overload, melusin-null hearts were subjected to chronic hypertension realized by surgical constriction of the transverse aorta as described below and in FIG. 6.

Mice were anesthetized by injection of a mixture of ketamine (100 mg/kg) and xylazine (10 mg/kg). After midline sthernotomy, the aortic arch is constricted between truncus anonimus and left carotid artery with 8-0 silk tied against the vessel and a blunted 27-gauge needle, which is promptly pulled out thereafter. In the control group the same surgical procedures are performed without constricting the aortic arch. Both wild type and melusin-null mice were subjected to the above surgical procedure. 7 days after surgery the degree of hemodynamic overload was evaluated as systolic pressure gradient measured by selective cannulation of left and right carotid arteries (Lembo et al. 1996)

After these hemodynamic evaluations, the mice are weighed, hearts excised and evaluation of cardiac hypertrophy obtained with left ventricular weight/body weight ratio.

While wild type mice develop an overt compensatory cardiac hypertrophy 7 days after surgery, melusin-null mice show only a very modest hypertrophy, evaluated by left ventricular/body weight ratio (FIG. 7).

To better characterize the evolution of the left ventricle remodeling during chronic pressure overload, melusin-null mice were subjected to TAC (transverse aortic constriction) for a period of 4 weeks and examined by serial echocardiographic analysis during this period. Cardiac structure and function were evaluated not invasively with transthoracic echocardiography in basal condition and after 2 and 4 weeks from TAC. All measurements were determined in a short axis view at the level of papillary muscles.

As expected, wild-type mice showed increased interventricular septum thickness and reduced end-distolic left ventricular diameters. In contrast, after 7 days of TAC, melusin-null mice developed only modest thickening of ventricular walls and a significant chamber enlargement (FIG. 8). After 2 weeks from TAC, melusin-null mice showed a further enlargement of left ventricular chamber as compared to that observed in wild-type mice (FIG. 11). After 4 weeks, left ventricular dilation was even more evident and associated with a marked deterioration of contractile function, as detected by the severe impairment of fractional shortening (FIG. 11). Finally, the lethality rates at 4 weeks from TAC were greater in mutant as compared to wild-type mice (53.3% vs 30.7%).

The absence of melusin results, thus, in reduced cardiac hypertrophy and promotes the left ventricle dilation when hearts are exposed to increased blood pressure. This condition is, thus, accelerating the onset of the defective cardiac response.

Example 3

Mechanosensor Role of Melusin in the Heart

To test whether melusin is involved in heart hypertrophy in response to stimuli different from pressure overload, the inventors also tested the cardiac response in melusin-null mice after chronic administration of phenylephrine or angiotensin II at sub-pressor doses which do not increase blood pressure.

Chronic administration of sub-pressor doses of phenylephrine (100 mg/kg/day) or angiotensin II (0,1 mg/kg/day) (Harada et al, 1998) was obtained by subcutaneous implantation of osmotic mini-pump (Alza Corp.) delivering the above doses of phenylephrine or angiotensin II for 21 days. In these experimental series control groups were treated with vehicle alone.

To verify that chronic agonists infusion does not alter blood pressure homeostasis, blood pressure profile was evaluated by radio-telemetric measurement realized through implantation of a commercially available device into the femoral artery and acquisition of the telemetered pressure signal in a dedicated, computed analysis system (Data Sciences International).

Cardiac hypertrophy was evaluated by left ventricular/body weight ratio. The results of these experiments indicate that melusin-null mice exposed to sub-pressor doses of phenylephrine or angiotensin II develop left ventricle hypertrophy in a manner not significantly different from wild type mice (FIG. 9).

These results altogether indicate that melusin is involved in the hypertrophic response to pressure overload (see Example 2), but is not required in the response to trophic factors such as phenylephrine or angiotensin II. This, thus, strongly points for a mechanosensor role of melusin in heart.

Example 4

The Lack of Melusin Impairs GSK3β Phosphorylation

To investigate the impact of melusin on cardiac intracellular signaling triggered by biomechanical stress, phosphorylation of signaling proteins reported to be involved in cardiac hypertrophy (Aoki and Izumo 2001; Hunter and Chien 1999; Hardt and Sadoshima, Circ Res. 2002) was analyzed.

Representative experiments are shown in FIG. 12. Wild-type (WT, empty bars) and melusin-null mice (KO, filled bars) were subjected to TAC for 10 min or to sham (S) operations as controls. Left ventricle protein extracts were analyzed by western blotting with antibodies to phosphorylated signaling molecules.

In particular the inventors found that glycogen synthase kinase 3beta (GSK3β) was differentially phosphorylated in wild type versus melusin-null mice. As shown in FIG. 12c, GSK3β was strongly phosphorylated at serine 9 residue 10 minutes after TAC in wild-type mice consistently with the hypothesis that this signal was triggered in response to a mechanical event. However, in melusin-null mice the degree of GSK3β serine 9 phosphorylation was severely reduced (FIG. 12c).

Since AKT is a major kinase regulating GSK3β serine 9 phosphorylation the inventors analyzed the phosphorylation state of this kinase. While AKT is rapidly phosphorylated in response to TAC in wild type mice, this response was strongly reduced in melusin-null mice (FIG. 12d).

GSK3β is involved in multiple signaling pathways and is a well known target of insulin receptor signaling (Cohen and Frame 2001). The inventors then tested whether the lack of melusin could affect GSK3β phosphorylation in response to insulin. Western blot analysis of heart extracts from mice treated for 10 and 20 min with insulin—administered with IP injections of 2IU—showed that GSK3β was phosphorylated at comparable level in both mice genotypes (FIG. 12e).

Since attenuation of cardiac hypertrophy in melusin-null mice was observed after 7 day TAC, the inventors then tested GSK3β signaling at this point in time. Interestingly GSK3β serine 9 phosphorylation was reduced in melusin-null mice versus wild type after 7 days of TAC (FIG. 12f). In addition kinase activity was increased as predicted by the inhibitory action of serine 9 phosphorylation (FIG. 12g). Thus altered GSK3β signaling is persistent in melusin-null mice exposed to 7 day TAC.

These data indicate that the lack of melusin selectively impairs left ventricular AKT and GSK3β phosphorylation in response to biomechanical stress.

Example 5

Isolation of Melusin-Agonist Organic Compound

In order to identify melusin agonists, molecules capable of activating melusin function have to be identified. Based on the previously published (Brancaccio et al 1999) and present data, integrins bind melusin and trigger its activation. Thus, peptides or organic compounds binding to melusin and interfering with melusin-integrin binding are expectedly good candidates as melusin agonists by mimicking the integrin-induced melusin activation. Such melusin agonists can be identified from a large library of peptide and peptide-like compounds by using the techniques of high-throughput screening using a well-defined assay for the detection of such agonists To this end, an ELISA assay can be used in which purified recombinant melusin, or fragments of the protein is adsorbed on the surface of microtiter wells are incubated with cell extracts containing integrin to allow integrin-melusin binding. To this mixture specific compounds are added to select molecules capable to bind melusin and prevent integrin binding. A similar procedure has already been used to select compound capable to interfere with integrin function in other cellular systems (Ambroise et al. 2002)

The following ELISA protocol can be used. Fusion proteins consisting GST (Glutathione S-trasferase) fused to the full-length human melusin and/or a fragment from amino acid residues 149-350 in the C-terminal region, containing the integrin binding site (Brancaccio et al 1999) are purified by affinity chromatography on glutathione-Sepharose 4B. Purified fusion proteins are adsorbed on microtiter wells according to standard procedures and used as ligands for integrin binding. COS cell extracts are used as source of beta1 integrin heterodimers.

Briefly COS cells are washed twice with cold PBS and extracted in TBS (25 mM Tris-HCl, pH 7.6, 150 mM NaCl, 1 mM NaVO4, 10 mM NaF, 10 μg/ml leupeptin, 4 μg/ml pepstatin and 0.1 TIU/ml aprotinin) 0.5% Nonidet P-40 plus 1 mM $Ca^{2+}$, or with TBS, 0.5% Nonidet P-40 plus 5 mM EDTA to solubilized membrane proteins. 100 μl of cell extracts containing 2 mg of proteins/ml are incubated overnight at 4° C. in wells coated with GST-melusin, GST-melusin(aa149-350) and GST alone (as control). After washing, integrin binding is detected with the TS2/16 monoclonal antibody followed by peroxidase-conjugated anti-mouse antibody. The compounds capable to interfere with integrin-melusin binding will be added at increasing concentrations together with the COS cell extract during the incubation with the GST-melusin fusion protein.

As source of compounds capable to interfere with melusin-integrin binding, random peptides phage display library can be used (Ladner and Ley 2001). In such libraries random oligonucleotide sequences coding for short amino acid sequences (8-18 residues) are inserted in the coding sequence of the phage coat proteins. The resulting phage displays on its surface the random peptide sequence to be selected for its binding capacity. The phage population displaying the random peptides is allowed to interact with recombinant melusin adsorbed on the surface of microtiter wells before incubation with integrins. Phages interfering with integrin binding are isolated and the peptide sequence coded for by the inserted random oligonucleotide will be determined by DNA sequencing.

As an alternative source of organic compounds capable to bind melusin interfering with integrin binding combinatorial chemistry libraries are used (Floyd et al. 1999; Ambroise et al. 2002; Toogood 2002).

The peptide sequences isolated with the procedure described above will be tested for their ability to trigger in vitro cardiomyocyte hypertrophy. For this test melusin-null cardiomyocytes derived from the trangenic animals of the invention are used to define the specificity of the isolated compound toward melusin. Such compound are ineffective on melusin-null cardiomycytes while they should be active on wild type cells.

To allow penetration in the cells, the peptides are coupled to trojan peptides (Derossi et al 1998) that allow spontaneous and efficient intracellular delivery.

Active peptides are also used to develop structural analog organic compounds more suitable for in vivo treatment.

Genetically modified mice models developing, either spontaneous or pressure overload-induced, dilated cardiomyopathy (for review see Chien, 1999) are treated by delivering peptide analogs with subcutaneous implantation of infusion mini-pumps and analyzed for their cardiac function and morphology to monitor the in vivo potential therapeutic activity of the compounds.

The same strategy is applied with molecules acting downstream of melusin in controlling the cardiac hypertrophy response. Using different experimental approaches, including co-immunoprecipitation, affinity chromatography and the two hybrid test, proteins binding to melusin and functioning as downstream transducers of the mechanochemical signal leading to hypertrophy can be identified (between step 2 and 3 in FIG. 10). Once these molecules are identified and characterized, the same strategy described above can be applied to select agonists that boost the activation of such proteins acting downstream of melusin. Such drugs are tested in melusin-null transgenic mice for their ability to rescue left ventricle dilation observed in these animals after TAC.

Example 6

Melusin Gene-Therapy to Prevent and Treat Heart Dilation and Failure

As discussed above an alternative therapeutic strategy to prevent and/or cure heart dilation and failure can be achieved by inducing over-expression of melusin.

Adenovirus constructs and/or other viral vectors such as lentiviral vectors have been proved efficient vector for gene delivery in experimental heart pathologies (Wright et al 2001). Adenoviral vector expressing the melusin gene are prepared according to the following protocol given as an example. Lentiviral vectors can be prepared by similar procedures as well.

Human melusin cDNA (GenBank AF140690) is cloned in a shuttle vector (pAdTrack-CMV) containing GFP marker. 100-500 ng of the resultant plasmid is linearized by digestion with PmeI restriction endonuclease, and after digestion extracted with phenol-cloroform treatment, precipitated with etanol and resuspended in 6 µl of deionised water. PmeI-digested shuttle plasmid is co-transformed with 100 ng of adenoviral backbone vector (pAdEasy-1) by electroporation in BJ5183 *E. coli* cells. Transformed *E. coli* cells are resuspended in 500 µl of L-broth, plated on 3 LB kanamycin plates and grown overnight at 37° C. 10-20 colonies are picked up and grown in 2 ml L-broth containing 25 µg/ml kanamycin for 10-15 hours. DNA minipreps are performed with conventional methods and supercoiled plasmids are digested with PacI restriction endonuclease. Candidate clones yield after digestion a large fragment of about 30 kb and a smaller one of 3 or 4.5 kb. Recombinant adenovirus is retransformed in *E. coli* and is purified using commercially available purifications kits. 4 µg of recombinant adenoviral DNA is then linearized wth PacI restriction endonuclease, precipitated with ethanol, resuspended in 20 µl of sterile water and used for transfection of $2 \times 10^6$ 293 cells (E1-transformed human embryonic kidney cells) at 50-70% confluence. Transfection and viral production is monitored by the fluorescent protein GFP expression. Cells are scraped with a rubber policeman at 7-10 days post-transfection and collected in 50 ml tubes, then spinned in a centrifuge and resuspended in 2 ml sterile PBS. Cells are frozen in dry ice-methanol bath and are thawed in a 37° C. water bath and then vortexed. Cells are frozen and thawed for a total of 4 cycles. Then samples are spinned briefly and stored at −20° C. This viral supernatant is used to infect 50-70% confluent 293 cells in order to produce large amount of viral stocks. The virus are collected when a third to half of the cells are detached. It is possible to confirm the virus presence using PCR and western blot analysis. Viral titer is measured by counting green fluorescent 293 cells 18 hours after infection with various dilutions of virus supernatant.

The adenoviral vector is delivered to animals following a catheter-based protocol for intracardiac injection according to Hajjar et al. (Hajjar et al 1998).

As proof of efficacy in vivo, the melusin adenoviral vector are tested for its ability to rescue cardiac dilation in melusin-null mice subjected to transverse aortic constriction. This procedure is also applied on different transgenic mouse models with impaired hypertrophy response, or with spontaneous dilated cardiomyopathy.

REFERENCES

Akhter S A, Luttrell L M, Rockman H A, Iaccarino G, Lefkowitz R J, Koch W J. Targeting the receptor-Gq interface to inhibit in vivo pressure overload myocardial hypertrophy. Science 1998 280:574-7

Ambroise Y, Yaspan B, Ginsberg M H, Boger D L. Inhibitors of Cell Migration that Inhibit Intracellular Paxillin/alpha4 Binding. A Well-Documented Use of Positional Scanning Libraries. Chem Biol. 2002; 9: 1219-26.

Aoki H and Izumo S. Signal transduction of cardiac myocyte hypertrophy. Heart Physiology and Pathophysiology, Fourth Edition, Capter 58 pages 1065-1086; Academic Press 2001.

Arber S, Hunter J J, Ross J Jr, Hongo M, Sansig G, Borg J. Perriard J C, Chien K R, Caroni P. MLP-deficient mice exhibit a disruption of cardiac cytoarchitectural organization, dilated cardiomyopathy, and heart failure. Cell. 1997; 88: 393-403.

Badorff C, Ruetten H, Mueller S, Stahmer M, Gehring D, Jung F, Ihling C, Zeiher A M, Dimmeler S. Fas receptor signaling inhibits glycogen synthase kinase 3 beta and induces cardiac hypertrophy following pressure overload. J Clin Invest. 2002; 109:373-81.

Belkin A M, Retta S F, Pletjushkina O Y, Balzac F, Silengo L, Fassler R, Koteliansky V E, Burridge K, Tarone G. Muscle beta1D integrin reinforces the cytoskeleton-matrix link: modulation of integrin adhesive function by alternative splicing. J Cell Biol 1997; 139:1583-95

Belkin A M, Zhidkova N I, Balzac F, Altruda F, Tomatis D, Maier A, Tarone G, Koteliansky V E, Burridge K. Beta 1D integrin displaces the beta 1A isoform in striated muscles: localization at junctional structures and signaling potential in nonmuscle cells. J Cell Biol 1996; 132:211-26

Brancaccio M, Guazzone S, Menini N, Sibona E, Hirsch E, De Andrea M, Rocchi M, Altruda F, Tarone G, Silengo L. J Biol Chem 1999; 274: 29282-8

Carson J A, Wei L. Integrin signaling's potential for mediating gene expression in hypertrophying skeletal muscle. J Appl Physiol. 2000, 88: 337-43

Chien K R, 1999, Cell 98; 555-558

Cohen P, Frame S. The renaissance of GSK3. Nat Rev Mol Cell Biol. 2001; 2: 769-76.

Davis M J, Wu X, Nurkiewicz T R, Kawasaki J, Davis G E, Hill M A, Meininger G A. Integrins and mechanotransduction of the vascular myogenic response. Am J Physiol Heart Circ Physiol. 2001, 280: H1427-33.

Derossi D, Chassaing G, Prochiantz A. Trojan peptides: the penetrating system for intracellular delivery. *Trends Cell Biol* 8:84-7, 1998

Floyd C D, Leblanc C, Whittaker M. Combinatorial chemistry as a tool for drug discovery. Prog Med. Chem. 1999; 36: 91-168.

Hajjar R J, Schmidt U, Matsui T, Guerrero J L, Lee K H, Gwathmey J K, Dec G W, Semigran M J, Rosenzweig A. Modulation of ventricular function through gene transfer in vivo. Proc Natl Acad Sci USA 1998, 95:5251-6

Harada K, Komuro I, Shiojima I, Hayashi D, Kudoh S, Mizuno T, Kijima K, Matsubara H, Sugaya T, Murakami K, Yazaki Y (1998) Pressure overload induces cardiac hypertrophy in angiotensin II type 1A receptor knockout mice. *Circulation;* 97: 1952-9

Hardt S E, Sadoshima J. Glycogen synthase kinase-3beta: a novel regulator of cardiac hypertrophy and development. Circ Res. 2002; 90:1055-63.

Hirota H, Chen J, Betz U A, Rajewsky K, Gu Y, Ross J Jr, Muller W, Chien K R Loss of a gp130 cardiac muscle cell survival pathway is a critical event in the onset of heart failure during biomechanical stress. Cell 1999, 97:189-98

Hasuwa H, Kaseda K, Einarsdottir T, Okabe M. Small interfering RNA and gene silencing in transgenic mice and rats. FEBS Lett 2002, 532:227-30

Hunter J J, Chien K R. Signaling pathways for cardiac hypertrophy and failure. N Engl J Med 1999, 341:1276-83

Ladner R C, Ley A. Novel frameworks as a source of high-affinity ligands. Curr Opin Biotechnol. 2001; 12: 406-410

Lembo G, Rockman H A, Hunter J J, Steinmetz H, Koch W J, Ma L, Prinz M P, Ross J Jr, Chien K R, Powell-Braxton L. (1996) Elevated blood pressure and enhanced myocardial contractility in mice with severe IGF-1 deficiency. *J Clin Invest;* 98: 2648-55

Ruwhof C, van der Laarse A. Mechanical stress-induced cardiac hypertrophy: mechanisms and signal transduction pathways. Cardiovasc Res 2000, 47:23-37

Toogood P L. Inhibition of protein-protein association by small molecules: approaches and progress. J Med. Chem. 2002; 45: 1543-58.

Wakasaki H, Koya D, Schoen F J, Jirousek M R, Ways D K, Hoit B D, Walsh R A, King G L Targeted overexpression of protein kinase C beta2 isoform in myocardium causes cardiomyopathy. Proc Natl Acad Sci USA 1997; 94:9320-5.

Wright M J, Wightman L M, Lilley C, de Alwis M, Hart S L, Miller A, Coffin R S, Thrasher A, Latchman D S, Marber M S. In vivo myocardial gene transfer: optimization, evaluation and direct comparison of gene transfer vectors. Basic Res Cardiol 2001, 96: 227-36.

The invention claimed is:

1. A transgenic mouse comprising a disruption in its endogenous melusin gene, wherein said mouse lacks expression of endogenous melusin, and wherein said mouse, after being subjected to a hypertensive condition, develops at least a phenotype selected from the group consisting of impaired heart hypertrophy, heart dilation, and heart failure.

2. The transgenic mouse according to claim 1, wherein said hypertensive condition is induced by surgical operation.

3. The transgenic mouse according to claim 2, wherein said surgical operation consists of surgical constriction of the transverse aorta.

4. The transgenic mouse according to claim 1, wherein said hypertensive condition is induced by pharmacological treatment.

5. The transgenic mouse according to claim 1, wherein said hypertensive condition is induced by high sodium diet.

6. The transgenic mouse according to claim 1, wherein said mouse develops at least impaired heart hypertrophy.

7. The transgenic mouse according to claim 1, wherein said mouse develops at least heart dilation.

8. The transgenic mouse according to claim 1, wherein said mouse develops at least heart failure.

9. The transgenic mouse according to claim 4, wherein said pharmacological treatment is administration of hypertensive drugs.

10. The transgenic mouse according to claim 1, wherein said mouse belongs to the 129SV, C57Bl or 129SVxC57Bl strain.

11. A method of selecting a compound that is pharmacologically active in the prevention of heart failure, said method comprising:
  i) administering compounds to the transgenic mouse according to claim 1,
  ii) inducing a hypertensive condition in said mouse, and
  iii) selecting a compound that is pharmacologically active in the prevention of heart failure.

12. A method of studying a heart pathology, said method comprising:
  i) exposing the transgenic mouse according to claim 1 to hypertensive conditions and
  ii) studying development of a heart pathology in said mouse, wherein said heart pathology is selected from the group consisting of heart failure, congestive heart failure, dilated cardiomyopathy, hypertensive cardiomyopathy, hypertrophic cardiomyopathy, and heart infarct.

13. Cells obtained from the transgenic mouse according to claim 1.

14. A method of selecting a compound that is pharmacologically active in the prevention of heart failure, said method comprising:
  i) administering compounds to the cells according to claim 13,
  ii) inducing a hypertensive condition in said cells, and
  iii) selecting a compound that is pharmacologically active in the prevention of heart failure.

15. A method of producing a transgenic mouse comprising a disruption in its endogenous melusin gene, wherein said mouse lacks expression of endogenous melusin, and wherein said mouse after being subjected to a hypertensive condition, develops at least a phenotype selected from the group consisting of impaired heart hypertrophy, heart dilation, and heart failure, said method comprising:
  (a) disrupting by homologous recombination the gene encoding melusin in a mouse embryonic stem (ES) cell,
  (b) injecting said ES cell into a mouse blastocyst,
  (c) implanting said blastocyst into the uterus of a foster mother mouse to generate a chimeric embryo,
  (d) obtaining a chimeric mouse which has germ line cells comprising a disrupted gene encoding melusin from said chimeric embryo,
  (e) breeding said chimeric mouse with a different mouse strain, and
  (f) selecting a male transgenic mouse comprising disruption of the gene encoding melusin.

16. The method according to claim 15, further comprising breeding said male transgenic mouse with a female transgenic mouse comprising a heterozygous or homozygous disruption in its endogenous melusin gene, and selecting a homozygous female mouse comprising disrupted genes encoding melusin.

17. A method of selecting a compound that is pharmacologically active in the treatment of heart failure, said method comprising:
  i) inducing a hypertensive condition in the transgenic mouse according to claim 1, ii) administering compounds to said mouse, and iii) selecting a compound that is pharmacologically active in the treatment of heart failure.

18. A method of selecting a compound that is pharmacologically active in the treatment of heart failure, said method comprising:

i) inducing a hypertensive condition in the cells according to claim 13, ii) administering compounds to the said cells, and iii) selecting a compound that is pharmacologically active in the treatment of heart failure.

* * * * *